US00PP22651P2

(12) United States Plant Patent
Snoeijer

(10) Patent No.: US PP22,651 P2
(45) Date of Patent: Apr. 17, 2012

(54) ***CLEMATIS* PLANT NAMED 'ZODAKI'**

(50) Latin Name: ***Clematis* hybrid**
Varietal Denomination: Zodaki

(76) Inventor: Wim Snoeijer, Gouda (NL)

( * ) Notice: Subject to any disclaimer, the term of this patent is extended or adjusted under 35 U.S.C. 154(b) by 0 days.

(21) Appl. No.: 12/924,454

(22) Filed: Sep. 28, 2010

(51) Int. Cl.
*A01H 5/00* (2006.01)

(52) U.S. Cl. ..... Plt./228

(58) Field of Classification Search ..... Plt./228
See application file for complete search history.

(56) References Cited

OTHER PUBLICATIONS

UPOV-ROM GTITM, Plant Variety Database, 2011/01, Pluto database, Citation for plant 'Zodaki'.*
UPOV-ROM GTITM, Plant Variety Database, 2011/04, GTI Jouve Retrieval Software, Citation for plant 'Zodaki'.*

* cited by examiner

*Primary Examiner* — Susan McCormick Ewoldt
(74) *Attorney, Agent, or Firm* — Penny J. Aguirre

(57) ABSTRACT

A new cultivar of hybrid *Clematis*, 'Zodaki', characterized by its floriferous habit, its flowers that are pale purple to pale violet in color with yellow centers, its uniform double flowers in both spring and summer, its upright facing flowers with good presentation, and its cold hardiness at least to U.S.D.A. Zone 6.

2 Drawing Sheets

Botanical classification: *Clematis* hybrid.
Variety denomination: 'Zodaki'.

BACKGROUND OF THE INVENTION

The present invention relates to a new and distinct cultivar of *Clematis*, botanically an interspecific hybrid, and will be referred to hereafter by its cultivar name 'Zodaki'. 'Zodaki' is grown as an herbaceous perennial for landscape use or as a terrace pot plant.

'Zodaki' was derived from seedlings raised by the Inventor from crossbreeding *Clematis* 'Mrs. George Jackman' (unpatented) pollinated by *Clematis* 'Piilu' (unpatented) in Boskoop, the Netherlands. The crossbreeding was done in 2000 and the seedling 'Zodaki' was selected as a single unique plant from the batch of seedlings in 2004.

Asexual reproduction of the new cultivar was first accomplished by internodial stem cuttings by the Inventor in Boskoop, The Netherlands in 2004. The characteristics of this cultivar have been determined to be stable and are reproduced true to type in successive generations.

SUMMARY OF THE INVENTION

The following traits have been repeatedly observed and represent the characteristics of the new cultivar as grown outdoors. These attributes in combination distinguish 'Zodaki' from other varieties of *Clematis* known to the Inventor.

1. 'Zodaki' exhibits a floriferous habit.
2. 'Zodaki' exhibits flowers that are pale purple to pale violet in color with yellow centers.
3. 'Zodaki' exhibits double flowers in both spring and summer.
4. 'Zodaki' exhibits upright facing flowers with good presentation.
5. 'Zodaki' exhibits flowers that are uniform in shape.
6. 'Zodaki' is cold hardy at least to U.S.D.A. 6.

'Zodaki' can be most closely compared to its parent plants. 'Mrs. George Jackman', the seed parent, differs primarily from 'Zodaki' in having single flowers and flowers that are creamy white in color with brown centers. 'Piilu', the pollen parent, differs primarily from 'Zodaki' in having flowers that are double only in the spring and are pink in color.

'Zodaki' can be compared to the cultivars 'Denny's Double' (not patented) and 'Belle of Woking' (not patented). 'Zodaki' exhibits flowers with tepal margins that are short wavy and exhibits flowers in both spring and summer. 'Denny's Double' differs from 'Zodaki' in having flowers that are twice the size, tepal margins that are smooth and in having very few flowers in summer. 'Belle of Woking' differs from 'Zodaki' in having tepal margins that are smooth and in typically not exhibiting any flowers in summer.

BRIEF DESCRIPTION OF THE DRAWING

The accompanying colored photographs illustrate the overall appearance and distinct characteristics of *Clematis* 'Zodaki'. The photographs were taken of plants of 'Zodaki' that were grown outdoors for three years in a trial bed in Boskoop, The Netherlands.

Figure 1:
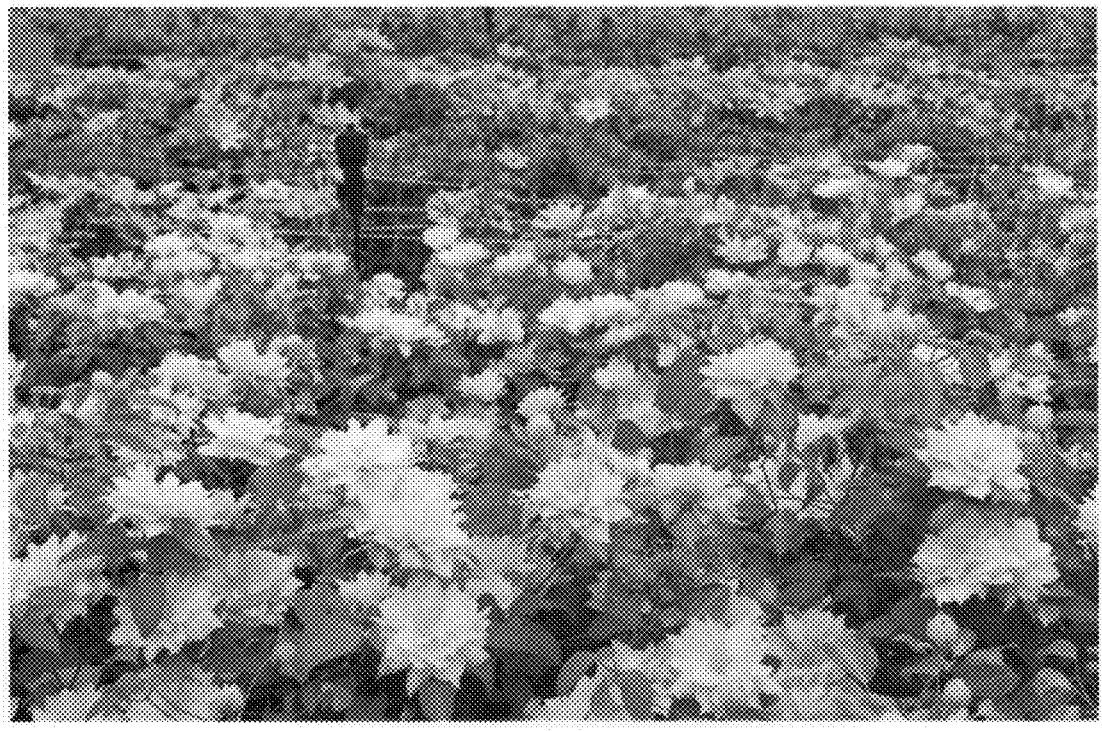
FIG. 1 shows the flowering habit of 'Zodaki'.
Figure 2:
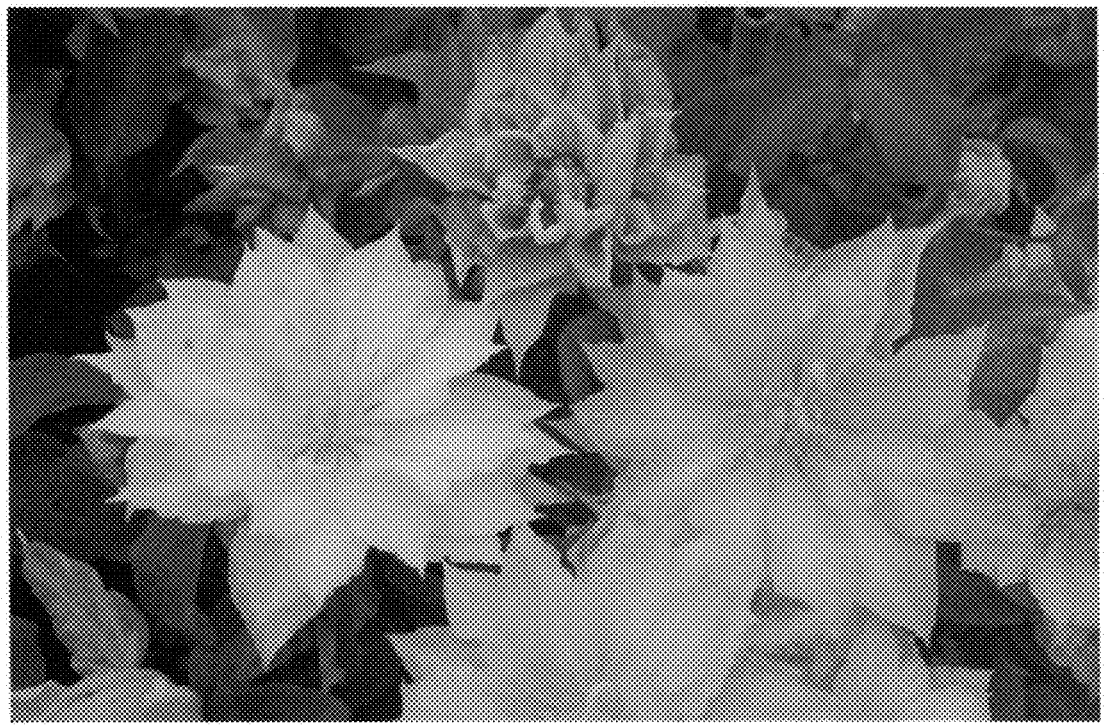
FIG. 2 shows summer flowers of 'Zodaki' with the stamens and pistils presented.
Figure 3:
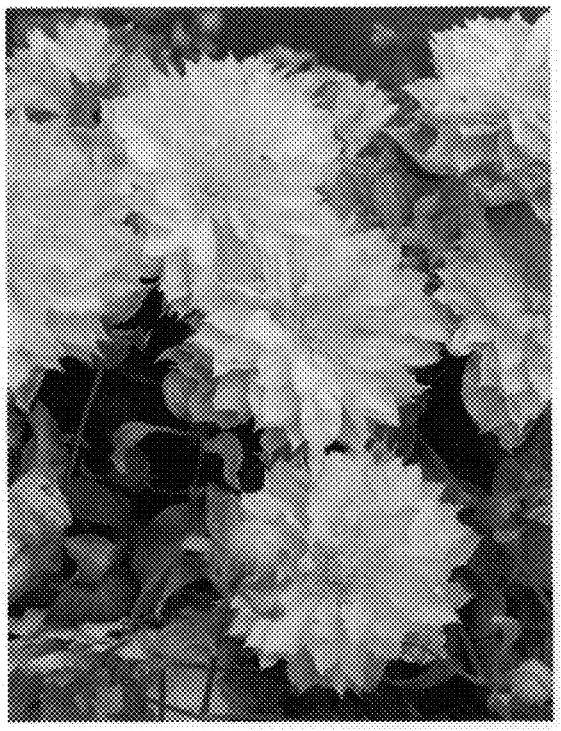
FIG. 3 shows spring flowers of 'Zodaki'.
Figure 4:
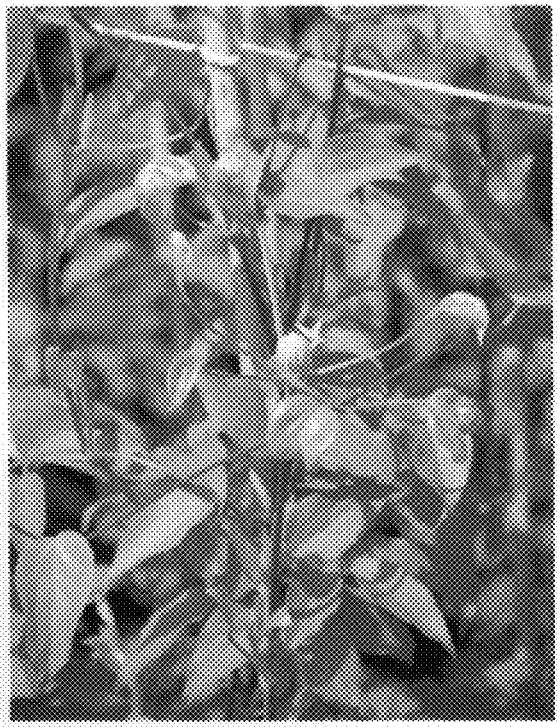
FIG. 4 shows a young shoot of 'Zodaki' with developing terminal flower bud.
Figure 5:
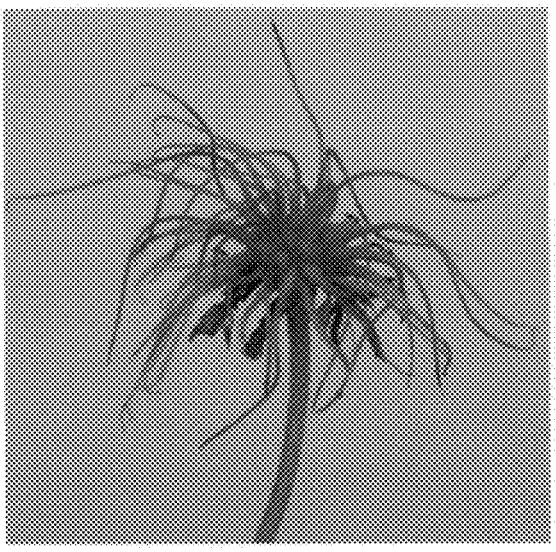
FIG. 5 shows a seedhead of 'Zodaki'.
Figure 6:
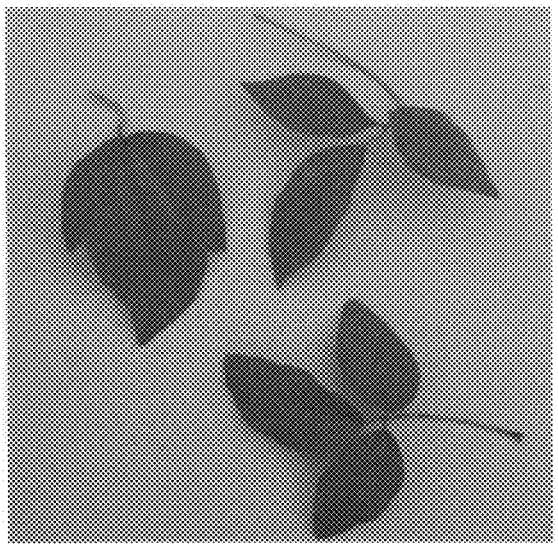
FIG. 6 shows 3 leaves of 'Zodaki'.

The colors of the photographs are as close as possible with the digital photography techniques available, the color values cited in the detailed botanical description describe the colors as accurately as possible of *Clematis* 'Zodaki'.

DETAILED BOTANICAL DESCRIPTION

The following is a detailed description of 3 year-old plants of *Clematis* 'Zodaki' as grown outdoors in full sun to semishade in a nursery in Boskoop, The Netherlands. The phenotype of *Clematis* 'Zodaki' may vary with variations in environmental, climatic and cultural conditions, as the cultivar has not been tested under all possible environmental conditions. The color determination is in accordance with The 2001 R.H.S. Colour Chart of The Royal Horticultural Society, London, England, except where general color terms of ordinary dictionary significance are used. The International Nomenclatural Standard is deposited at the Nationaal Herbarium Nederland, Leiden Branch (L).

General description:

*Botanical classification*.—'Zodaki' is an interspecific hybrid of *Clematis*.

*Common name*.—'Zodaki' *Clematis*.

*Parentage*.—Hybrid derived from the female parent *Clematis* 'Mrs George Jackman', pollinated by *Clematis* 'Piilu'.

*Blooming period*.—Flowering for 4 to 6 weeks in spring and 6 to 8 weeks in summer.

*Plant habit*.—Herbaceous climber.

*Height*.—Three year-old plant will reach about 2 m height.

*Cold hardiness*.—At least to U.S.D.A. Zone 6.

*Culture*.—Moist but well-drained soil in full sun with the roots in the shade.

*Diseases and pests*.—Susceptibility to wilt has not been determined.

*Root description*.—Fleshy.

Growth and propagation:

*Propagation*.—Internodial soft wood cuttings from vegetative shoots.

*Root initiation*.—Roots develop in 6 weeks in summer under greenhouse conditions.

*Time required for root development*.—75 to 90 days to develop a 5 cm container from a 5 cm cutting.

*Growth rate*.—Moderately vigorous once planted out.

Stem description:

*Shape*.—Round, 6 ribbed.

*Stem color*.—When young green 141B suffused with purple 59B in color but quickly dark woody brown 165A.

*Stem size*.—About 2 m in length, an average of 5 mm in diameter.

*Stem surface*.—Sparsely hairy with hairy nodes.

*Branching*.—Basal branches.

Foliage description:

*Leaf arrangement*.—Opposite.

*Leaf division*.—Primarily ternate.

*Internode length*.—Up to 10 cm.

*Leaf size*.—Up to 10 cm in length and 8 cm in width.

*Leaflet shape*.—Broadly ovate.

*Leaflet base*.—Obtuse.

*Leaflet apex*.—Acuminate.

*Leaflet fragrance*.—None.

*Leaflet venation*.—Primarily reticulate, more prominent on lower surface, color matches leaf color.

*Leaflet margins*.—Entire.

*Leaflet attachment*.—Petiolulate with leaf petiolate.

*Leaflet surface*.—Upper surface glabrous with main veins sparsely hairy, lower surface hairy or sparsely throughout, slightly glossy.

*Leaflet size*.—Up to 7 cm in length and 4 cm in width.

*Leaflet color*.—Upper surface dark green 141A in color, lower surface paler green 141C in color.

*Petioles and petiolules*.—2 to 10 cm in length and 1 to 2 mm in width, curling, slightly ribbed, sparsely hairy to subglabrous surface, dark green 141A in color.

Inflorescence description:

*Inflorescence type*.—Solitary flowers in spring, in summer an almost panicle-like inflorescence with 3 to 7 flowers.

*Inflorescence arrangement*.—Terminal in spring, terminal and axillary in summer.

*Inflorescence size*.—Ranges from an average of 9 cm in diameter and 5 cm in depth when a single flower and an average of about 25 cm in diameter and 10 cm in depth when in panicles.

*Peduncles*.—3 to 10 cm in length and about 3 mm in width, round in shape and 12-ribbed, surface hairy to villous near the flower, strong, held upright, 138B in color.

*Flower bud description*.—Upright, orbicular in shape and quickly opening from the base, 155C in color.

*Flower fragrance*.—None.

*Lastingness of the flowers*.—Individual flowers last about 12 days.

*Flower quantity*.—About 20 to 40 flowers on a 3 year old established plant.

*Flower type*.—Ball-shaped in spring flowers, summer flowers slightly more spreading.

*Flower aspect*.—Upright facing.

*Flower size*.—Range from 8 to 10 cm in diameter and about 5 cm in depth.

*Flower sex*.—Bisexual.

*Tepal-like staminodes and tepal-like pistils number*.—Up to 80 in spring flowers, up to 40 in summer flowers.

*Tepal-like stamens and tepal-like pistils shape*.—Lanceolate.

*Tepal-like stamens and tepal-like pistils apex*.—Acute.

*Tepal-like stamens and tepal-like pistils base*.—Cuneate.

*Tepal-like stamens and tepal-like pistils margins*.—Entire but short wavy when young.

*Tepal-like stamens and tepal-like pistils surface*.—Upper surface glabrous, lower surface villous with glabrous margin.

*Tepal-like stamens and tepal-like pistils color*.—In spring flowers pale purple 76D to pale violet 85D in color, summer flowers are more pale violet-blue 97C to pale violet-blue 92D in color.

*Tepal-like stamens and tepal-like pistils size*.—Up to 4 cm in length and 1.5 cm in width.

Reproductive organs:

*Gynoecium*.—Numerous pistils 20, up to 1 cm in length, ovary superior and greenish 145D in color, style silvery 198D plumose with long hairs, stigma dull white 155D and glabrous.

*Androcoecium*.—Stamens about 20 on spring flowers, up to 100 on summer flowers, 0.7 to 1.2 cm in length, filaments are 0.3 to 0.9 cm in length and 0.01 cm in width, pale yellow in color 4D, linear and glabrous, anthers are 0.3 to 0.5 cm in length, filiform, pale cream in color 155D, connective yellow in color 4C, glabrous and very short obtuse elongated.

*Seed*.—Seed head when pollinated is up to 4 cm in diameter and depth, usually remains of the tepal-like stamens and tepal-like pistils present, achene is green 138B, style green 138B with brown hairs 200D, up to 2.5 cm in length, stigma is black in color (202A) and bend.

It is claimed:

1. A new and distinct cultivar of *Clematis* plant named 'Zodaki' as herein illustrated and described.

* * * * *